United States Patent
Bae et al.

(10) Patent No.: US 10,143,727 B2
(45) Date of Patent: Dec. 4, 2018

(54) METHOD USING AN Y1 RECEPTOR ACTIVATOR FOR TREATING AN ANTICANCER AGENT-INDUCED NEPHROTOXIC INJURY

(71) Applicant: KYUNGPOOK NATIONAL UNIVERSITY INDUSTRY-ACADEMIC COOPERATION FOUNDATION, Daegu (KR)

(72) Inventors: Jae Sung Bae, Daegu (KR); Hee Kyung Jin, Daegu (KR); Min Hee Park, Gyeongsangbuk-do (KR)

(73) Assignee: KYUNGPOOK NATIONAL UNIVERSITY INDUSTRY-ACADEMIC COOPERATION FOUNDATION (KR)

( * ) Notice: Subject to any disclaimer, the term of this patent is extended or adjusted under 35 U.S.C. 154(b) by 0 days.

(21) Appl. No.: 15/424,185

(22) Filed: Feb. 3, 2017

(65) Prior Publication Data

US 2017/0224781 A1    Aug. 10, 2017

(30) Foreign Application Priority Data

Feb. 5, 2016   (KR) .................. 10-2016-0015094

(51) Int. Cl.
  *A61K 38/00*   (2006.01)
  *A61K 38/22*   (2006.01)
(52) U.S. Cl.
  CPC ................. *A61K 38/2271* (2013.01)
(58) Field of Classification Search
  None
  See application file for complete search history.

(56) References Cited

FOREIGN PATENT DOCUMENTS

KR    20140027833 A    3/2014

OTHER PUBLICATIONS

Clarke et al, Coronary Artery Infusion of Neuropeptide Y in Patients with Angina Pectoris, The Lancet, May 9, 1987, pp. 1057-1059, Divisions of Cardiology and Endocrinology, Royal Postgraduate Medical School, Hammersmith Hospital, London, United Kingdom.
Pabla et al, Inhibition of PKC reduces cisplatin-induced nephrotoxicity without blocking chemotherapeutic efficacy in mouse models of cancer, The Journal of Clinical Investigation, Jul. 2011, pp. 2709-2722, vol. 121 No. 7, American Society for Clinical Investigation, Ann Arbor, Michigan.
Jiang et al, Role of p53 in cisplatin-induced tubular cell apoptosis: dependence on p53 transcriptional activity, American Journal of Physiology Renal Physiology, Aug. 17, 2004, pp. F1140-F1147, vol. 287, American Physiological Society, Bethesda, Maryland.
Santos-Carvalho et al, Neuropeptide Y receptors activation protects rat retinal neural cells against necrotic and apoptotic cell death induced by glutamate, Cell Death and Disease (2013) 4, May 16, 2013, pp. 1-13, edition 636, Macmillan Publishers Limited, London, United Kingdom.
Hu et al, Knockdown of microtubule actin crosslinking factor 1 inhibits cell proliferation in MC3T3-E1 osteoblastic cells, BMB Reports, 2015, pp. 583-588, vol. 48 No. 10, The Korean Society for Biochemistry and Molecular Biology, Seoul, South Korea.
Kim et al, Neuropeptide Y protects cisplatin-induced nephrotoxicity by regulating the p53-dependent apoptosis pathway, BMB Reports, Jan. 5, 2016, pp. 1-24, The Korean Society for Biochemistry and Molecular Biology, Seoul, South Korea.

*Primary Examiner* — Elly-Gerald Stoica
(74) *Attorney, Agent, or Firm* — Levenfeld Pearlstein, LLC

(57) ABSTRACT

There is provided a method for treating or reducing an anticancer agent-induced nephrotoxic injury, the method comprising the step of administering a Y1 receptor activator in an amount effective to treat or reduce the anticancer agent-induced nephrotoxic injury in a subject. Further, there is provided a method for screening an agent for treating or reducing an anticancer agent-induced nephrotoxic injury, the method comprising (a) applying a candidate material to a test sample of renal tissues or cells; and (b) identifying a Y1 receptor signaling in the test sample of renal tissues or cells.

3 Claims, 8 Drawing Sheets

Specification includes a Sequence Listing.

SEQUENCE LISTING

```
<160> NUMBER OF SEQ ID NOS: 28

<210> SEQ ID NO 1
<211> LENGTH: 36
<212> TYPE: PRT
<213> ORGANISM: Artificial Sequence
<220> FEATURE:
<223> OTHER INFORMATION: Human Neuropeptide Y(NPY)

<400> SEQUENCE: 1

Tyr Pro Ser Lys Pro Asp Asn Pro Gly Glu Asp Ala Pro Ala Glu Asp
 1               5                   10                  15

Met Ala Lys Tyr Tyr Ser Ala Leu Arg His Tyr Ile Asn Leu Ile Thr
            20                  25                  30

Arg Gln Arg Tyr
        35

<210> SEQ ID NO 2
<211> LENGTH: 36
<212> TYPE: PRT
```

<213> ORGANISM: Artificial Sequence
<220> FEATURE:
<223> OTHER INFORMATION: Human Peptide YY(PYY)

<400> SEQUENCE: 2

Tyr Pro Ile Lys Pro Glu Ala Pro Gly Glu Asp Ala Ser Pro Glu Glu
 1               5                  10                  15

Leu Asn Arg Tyr Tyr Ala Ser Leu Arg His Tyr Leu Asn Leu Val Thr
            20                  25                  30

Arg Gln Arg Tyr
         35

<210> SEQ ID NO 3
<211> LENGTH: 20
<212> TYPE: DNA
<213> ORGANISM: Artificial Sequence
<220> FEATURE:
<223> OTHER INFORMATION: Neuropeptide Y(NPY) Forward

<400> SEQUENCE: 3
agatccagcc ctgagacact                                            20

<210> SEQ ID NO 4
<211> LENGTH: 20
<212> TYPE: DNA
<213> ORGANISM: Artificial Sequence
<220> FEATURE:
<223> OTHER INFORMATION: Neuropeptide Y(NPY) Reverse

<400> SEQUENCE: 4
agatgagggt ggaaacttgg                                            20

<210> SEQ ID NO 5
<211> LENGTH: 20
<212> TYPE: DNA
<213> ORGANISM: Artificial Sequence
<220> FEATURE:
<223> OTHER INFORMATION: Y1 receptor(Y1R) Forward

<400> SEQUENCE: 5
tgtcaccaac attctgatcg                                            20

<210> SEQ ID NO 6
<211> LENGTH: 20
<212> TYPE: DNA
<213> ORGANISM: Artificial Sequence
<220> FEATURE:
<223> OTHER INFORMATION: Y1 receptor(Y1R) Reverse

<400> SEQUENCE: 6
gatgagaacc agcgagaaaa                                            20

<210> SEQ ID NO 7
<211> LENGTH: 20
<212> TYPE: DNA
<213> ORGANISM: Artificial Sequence
<220> FEATURE:
<223> OTHER INFORMATION: Y2 receptor(Y2R) Forward

<400> SEQUENCE: 7
tgcagacctc ccattgtatt                                            20

<210> SEQ ID NO 8
<211> LENGTH: 20
<212> TYPE: DNA

-continued

```
<213> ORGANISM: Artificial Sequence
<220> FEATURE:
<223> OTHER INFORMATION: Y2 receptor(Y2R) Reverse

<400> SEQUENCE: 8
caatccaagc atcggtaatc                                        20

<210> SEQ ID NO 9
<211> LENGTH: 20
<212> TYPE: DNA
<213> ORGANISM: Artificial Sequence
<220> FEATURE:
<223> OTHER INFORMATION: Y4 receptor(Y4R) Forward

<400> SEQUENCE: 9
tagtcgtgtc tgggcttttc                                        20

<210> SEQ ID NO 10
<211> LENGTH: 20
<212> TYPE: DNA
<213> ORGANISM: Artificial Sequence
<220> FEATURE:
<223> OTHER INFORMATION: Y4 receptor(Y4R) Reverse

<400> SEQUENCE: 10
agcaaagggc taaaccatct                                        20

<210> SEQ ID NO 11
<211> LENGTH: 27
<212> TYPE: DNA
<213> ORGANISM: Artificial Sequence
<220> FEATURE:
<223> OTHER INFORMATION: Y5 receptor(Y5R) Forward

<400> SEQUENCE: 11
gggctctata catttgtaag tcttctg                                27

<210> SEQ ID NO 12
<211> LENGTH: 27
<212> TYPE: DNA
<213> ORGANISM: Artificial Sequence
<220> FEATURE:
<223> OTHER INFORMATION: Y5 receptor(Y5R) Reverse

<400> SEQUENCE: 12
catggctttg ccgaacatcc actgatc                                27

<210> SEQ ID NO 13
<211> LENGTH: 20
<212> TYPE: DNA
<213> ORGANISM: Artificial Sequence
<220> FEATURE:
<223> OTHER INFORMATION: Y6 receptor(Y6R) Forward

<400> SEQUENCE: 13
ggagggatgg ttattgtgac                                        20

<210> SEQ ID NO 14
<211> LENGTH: 20
<212> TYPE: DNA
<213> ORGANISM: Artificial Sequence
<220> FEATURE:
<223> OTHER INFORMATION: Y6 receptor(Y6R) Reverse

<400> SEQUENCE: 14
gttgttgctc ttgccactgg                                        20
```

<210> SEQ ID NO 15
<211> LENGTH: 21
<212> TYPE: DNA
<213> ORGANISM: Artificial Sequence
<220> FEATURE:
<223> OTHER INFORMATION: P53 Forward

<400> SEQUENCE: 15
tgaaacgccg acctatcctt a       21

<210> SEQ ID NO 16
<211> LENGTH: 21
<212> TYPE: DNA
<213> ORGANISM: Artificial Sequence
<220> FEATURE:
<223> OTHER INFORMATION: P53 Reverse

<400> SEQUENCE: 16
ggcacaaaca cgaacctcaa a       21

<210> SEQ ID NO 17
<211> LENGTH: 20
<212> TYPE: DNA
<213> ORGANISM: Artificial Sequence
<220> FEATURE:
<223> OTHER INFORMATION: Bax Forward

<400> SEQUENCE: 17
ttgctacagg gtttcatcca       20

<210> SEQ ID NO 18
<211> LENGTH: 23
<212> TYPE: DNA
<213> ORGANISM: Artificial Sequence
<220> FEATURE:
<223> OTHER INFORMATION: Bax Reverse

<400> SEQUENCE: 18
catattgctg tccagttcat ctc       23

<210> SEQ ID NO 19
<211> LENGTH: 20
<212> TYPE: DNA
<213> ORGANISM: Artificial Sequence
<220> FEATURE:
<223> OTHER INFORMATION: Noxa Forward

<400> SEQUENCE: 19
actgtggttc tggcgcagat       20

<210> SEQ ID NO 20
<211> LENGTH: 21
<212> TYPE: DNA
<213> ORGANISM: Artificial Sequence
<220> FEATURE:
<223> OTHER INFORMATION: Noxa Reverse

<400> SEQUENCE: 20
ttgagcacac tcgtccttca a       21

<210> SEQ ID NO 21
<211> LENGTH: 21
<212> TYPE: DNA
<213> ORGANISM: Artificial Sequence
<220> FEATURE:

<223> OTHER INFORMATION: Puma Forward

<400> SEQUENCE: 21
atgcctgcct caccttcatc t                                    21

<210> SEQ ID NO 22
<211> LENGTH: 22
<212> TYPE: DNA
<213> ORGANISM: Artificial Sequence
<220> FEATURE:
<223> OTHER INFORMATION: Puma Reverse

<400> SEQUENCE: 22
agcacaggat tcacagtctg ga                                   22

<210> SEQ ID NO 23
<211> LENGTH: 21
<212> TYPE: DNA
<213> ORGANISM: Artificial Sequence
<220> FEATURE:
<223> OTHER INFORMATION: Bcl2 Forward

<400> SEQUENCE: 23
ttataagctg tcacagaggg g                                    21

<210> SEQ ID NO 24
<211> LENGTH: 25
<212> TYPE: DNA
<213> ORGANISM: Artificial Sequence
<220> FEATURE:
<223> OTHER INFORMATION: Bcl2 Reverse

<400> SEQUENCE: 24
gaactcaaag aaggccacaa tcctc                                25

<210> SEQ ID NO 25
<211> LENGTH: 22
<212> TYPE: DNA
<213> ORGANISM: Artificial Sequence
<220> FEATURE:
<223> OTHER INFORMATION: Mcl1 Forward

<400> SEQUENCE: 25
gaggaggaag aggacctata cc                                   22

<210> SEQ ID NO 26
<211> LENGTH: 25
<212> TYPE: DNA
<213> ORGANISM: Artificial Sequence
<220> FEATURE:
<223> OTHER INFORMATION: Mcl1 Reverse

<400> SEQUENCE: 26
agtttctgct aatggttcga tgaag                                25

<210> SEQ ID NO 27
<211> LENGTH: 22
<212> TYPE: DNA
<213> ORGANISM: Artificial Sequence
<220> FEATURE:
<223> OTHER INFORMATION: GAPDH Forward

<400> SEQUENCE: 27
tggcaaagtg gagattgttg cc                                   22

```
<210> SEQ ID NO 28
<211> LENGTH: 21
<212> TYPE: DNA
<213> ORGANISM: Artificial Sequence
<220> FEATURE:
<223> OTHER INFORMATION: GAPDH Reverse

<400> SEQUENCE: 28
aagatggtga tgggcttccc g                                          21
```

METHOD USING AN Y1 RECEPTOR ACTIVATOR FOR TREATING AN ANTICANCER AGENT-INDUCED NEPHROTOXIC INJURY

CROSS-REFERENCE TO RELATED APPLICATIONS

The present application claims a priority from Korean Patent Application No. 10-2016-0015094 filed on Feb. 5, 2016. The disclosures of the said application are incorporated by reference if fully set forth herein.

BACKGROUND

Technical Field

Exemplary embodiments relate to a pharmaceutical composition for preventing or treating a renal disease, the composition comprising Neuropeptide Y as an active ingredient. Another exemplary embodiments relate to a pharmaceutical composition for preventing or treating a renal disease, the composition comprising a Y1 receptor activator as an active ingredient. Still another exemplary embodiments relate to a method for treating or reducing an anticancer agent-induced nephrotoxic injury, the method comprising the step of administering a Y1 receptor activator in an amount effective to treat or reduce the anticancer agent-induced nephrotoxic injury in a subject. Still another exemplary embodiments relate to a method for screening an agent for treating or reducing an anticancer agent-induced nephrotoxic injury, the method comprising (a) applying a candidate material to a test sample of renal tissues or cells; and (b) identifying a Y1 receptor signaling in the test sample of renal tissues or cells.

Discussion of the Background

The kidneys are two organs found on the left and right sides of the body in vertebrates. Each kidney is made up of about 1 million nephrons as a basic structure, while a nephron carries out its functions of filtering and reabsorbing and is composed of fine capillary masses called glomeruli and renal tubules.

A renal disease refers to a condition in which the physiological functions of the kidneys in terms of excretion, regulation, metabolism and endocrinology are either entirely deteriorated or abnormal.

The renal disease may be classified, but is not limited to, as acute renal dysfunction or chronic renal failure according to its progression; diabetic nephropathy caused by complications such as glomerulonephritis due to deposition of vascular complex, diabetes and hypertension; toxic nephropathy caused by administration of drugs such as antibiotics and anticancer drugs; and urinary tract infection caused by bacterial infection. Regardless of the cause of the renal disease, if the renal abnormality chronically progresses and the glomerular filtration rate is reduced to less than 50%, the glomerular filtration rate continuously decreases in most cases, eventually reaching the end-stage renal dysfunction in which complications such as hematologic abnormalities, nervous system complications, gastrointestinal complications, immunological complications, infection and bone dystrophy occur and, in severe cases, lead to death.

The occurrence of the renal disease is increasing around the world every year. Further, since its symptoms do not appear or are unnoticed in many cases, it often leads to an end-stage renal dysfunction upon its detection. There are about 450,000 patients with renal dysfunction in the Republic of Korea, while it is expected to have more patients afflicted with renal disease in consideration of patients with early-stage renal dysfunction.

Regarding the treatment of renal dysfunction, although there are treatment methods such as long-term dialysis and renal transplantation, those methods do not provide means for treating the early-stage and mid-stage problems of chronic renal dysfunction. Moreover, the cost of treatment is significantly high, causing a serious financial burden on the country and patient families.

Accordingly, a safe and effective agent for treating a renal disease and a method for screening such a therapeutic agent are urgently required.

The above information disclosed in this Background section is only for enhancement of understanding of the background of the inventive concept, and, therefore, it may contain information that does not form the prior art that is already known in this country to a person of ordinary skill in the art.

SUMMARY

This Summary lists several embodiments of the presently disclosed subject matter. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features. Additional embodiments will be apparent from the disclosure, or may be learned by practice of the inventive concept.

In one embodiment, the presently disclosed subject matter provides a pharmaceutical composition for preventing or treating a renal disease, the composition comprising Neuropeptide Y as an active ingredient.

In another embodiment, the presently disclosed subject matter provides a food composition for preventing or ameliorating a renal disease, the composition comprising Neuropeptide Y as an active ingredient.

In another embodiment, the presently disclosed subject matter provides a pharmaceutical composition for preventing or treating a renal disease, the composition comprising a Y1 receptor activator as an active ingredient.

In another embodiment, the presently disclosed subject matter provides a food composition for preventing or ameliorating a renal disease, the composition comprising a Y1 receptor activator as an active ingredient.

In still another embodiment, the presently disclosed subject matter provides a method for treating or reducing an anticancer agent-induced nephrotoxic injury, the method comprising the step of administering a Y1 receptor activator in an amount effective to treat or reduce the anticancer agent-induced nephrotoxic injury in a subject.

In still another embodiment, the Y1 receptor activator is a substance selected from the group consisting of a ligand, a chemical compound, a peptide, a protein and a natural substance which is capable of activating a Y1 receptor signaling.

In still further embodiment, the Y1 receptor activator is a Y1 receptor agonist.

In still further embodiment, the Y1 receptor agonist is at least one selected from the group consisting of Neuropeptide Y (NPY), [Leu31Pro34]NPY, [D-Arg25]NPY, Peptide YY (PYY), $PYY_{3-36}$, $PYY_{1-36}$, and [Leu31, Pro34]PYY.

In still further embodiment, the Y1 receptor agonist is Neuropeptide Y (NPY) or [Leu31Pro34]NPY.

In still further embodiment, Neuropeptide Y (NPY) or [Leu31Pro34]NPY inhibits p53-dependent apoptosis.

In still further embodiment, the anticancer agent is at least one selected from the group consisting of cisplatin, doxorubicin, etoposide, paclitaxel, docetaxel, fluoropyrimidine, oxaliplatin, campthotecan, Belotecan, podophyllotoxin, vinblastine sulfate, cyclophosphamide, actinomycin, vincristine sulfate, methotrexate, bevacuzumab, thalidomide, eriotinib, gefitinib, camptothecin, Tamoxifen, Anasterozole, Gleevec, 5-fluorouracil (5-FU), Floxuridine, Leuprolide, Flutamide, Zoledronate, Vincristine, Gemcitabine, Streptozocin, Carboplatin, Topotecan, Irinotecan, Vinorelbine, hydroxyurea, Valrubicin, retinoic acid, Meclorethamine, Chlorambucil, Busulfan, Doxifluridine, Vinblastin, Mitomycin, Prednisone, Testosterone, Mitoxantron, aspirin, salicylates, ibuprofen, naproxen, fenoprofen, indomethacin, phenylbutazone, cyclophosphamide, mechlorethamine, dexamethasone, prednisolone, celecoxib, valdecoxib, nimesulide, cortisone, and corticosteroid.

In still another embodiment, the presently disclosed subject matter provides a method for screening an agent for treating or reducing an anticancer agent-induced nephrotoxic injury, the method comprising (a) applying a candidate material to a test sample of renal tissues or cells; and (b) identifying a Y1 receptor signaling in the test sample of renal tissues or cells.

BRIEF DESCRIPTION OF THE DRAWINGS

FIG. 1A depicts an experimental design to investigate the effect of Neuropeptide Y (NPY) on cisplatin-induced renal injury.

FIG. 1B is a graph demonstrating the expression level of Neuropeptide Y (NPY) in the kidney of PBS- or cisplatin-treated mice in each group (n=5 mice per group).

FIG. 1C and FIG. 1D are graphs showing the measured levels of BUN and creatinine where blood samples were collected three days after cisplatin treatment, respectively, in each group (scale bar: 20 μm; n=5 mice per group).

FIG. 1E shows the results of tubular damages and histological observation on renal tissues by H&E staining (*p<0.05). All error bars indicate S.E.M. All expression levels were normalized against GAPDH mRNA expression.

FIG. 2A shows representative immunofluorescence images of the kidneys showing apoptosis (TUNEL-positive nuclei, scale bar: 70 μm).

FIG. 2B depicts the results of the quantitative real-time PCR analysis showing the expression levels of pro-apoptotic or anti-apoptotic genes in renal tissues of each group (n=5 mice per group).

FIG. 2C shows the results of Western blot analysis and quantification of p53, Bax, and Bcl2 levels in the renal tissues of each group (n=6 mice per group) (*p<0.05). All error bars indicate S.E.M. All expression levels were normalized against GAPDH mRNA expression.

FIG. 3A is a graph depicting the expression levels of Y receptors in the renal tissues (Y1R, Y2R, Y4R, Y5R, and Y6R) (n=5 mice per group).

FIG. 3B and FIG. 3C show the levels of BUN and serum creatinine measured after the treatment of cisplatin and Y1 receptor agonist, respectively, in each group (n=5 mice per group).

FIG. 3D shows the results of tubular damages and histological observation on renal tissues by H&E staining (scale bar: 20 μm; n=5 mice per group).

FIG. 3E shows the results of TUNEL assay examining apoptosis in renal tissues. Representative images of TUNEL staining are shown (original magnification—400×, scale bar: 70 μm), together with the quantification of TUNEL-positive cells in renal tissues at each condition (n=5 mice per group).

FIG. 3F depicts the results of the quantitative real-time PCR analysis showing the expression levels of pro-apoptotic or anti-apoptotic genes (P53, Bax, Noxa, Puma, Bcl2, Mcl1) in renal tissues of each group (n=5 mice per group).

FIG. 3G shows the results of Western blot analysis and quantification of p53, Bax, and Bcl2 levels in the renal tissues of each group (n=6 mice per group) (*p<0.05). All error bars indicate S.E.M. All expression levels were normalized against GAPDH mRNA expression.

DETAILED DESCRIPTION OF THE ILLUSTRATED EMBODIMENTS

Figure 1A:
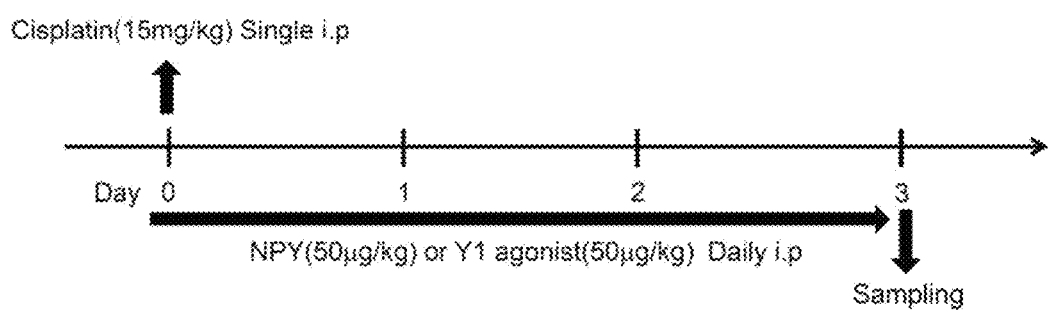
FIGS. 1A-1E show the effect of Neuropeptide Y (NPY) on cisplatin-induced renal injury.

The presently disclosed subject matter will be described more fully hereinafter with reference to the accompanying Examples and Drawings, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments of those skilled in the art.

It will be apparent to one skilled in the art that various modifications and variations can be made in the present invention without departing from the spirit or scope of the invention. Thus, it is intended that the present invention covers the modifications and variations of the presently described embodiments come within the scope of the appended claims and their equivalents.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

In some embodiments, the presently disclosed subject matter provides a pharmaceutical composition for preventing or treating a renal disease, the composition comprising Neuropeptide Y as an active ingredient.

As used herein, "Neuropeptide Y (NPY)" is a 36-amino acid peptide which belongs to a family of neuroendocrine peptide which becomes a pancreatic polypeptide. This peptide is abundant in the central and peripheral nervous systems of mammals, especially the hypothalamus and the cerebral cortex. It is known that Neuropeptide Y (NPY) exerts a wide range of physiological effects potentially in the therapeutic field and is likely to induce vasoconstriction and cause angina when administered alone (See Clarke, et al., Lancet 1 (8541):1057(1987)). In addition, Neuropeptide Y (NPY) is a neurotransmitter distributed in the central and peripheral nervous systems, which is known to increase in starvation, leading to an increase in appetite and a decrease in energy metabolism. However, there has been no report that Neuropeptide Y (NPY) can improve or ameliorate the side effects of anticancer drugs. In addition, Neuropeptide Y as used herein is not limited in terms of its origin, while encompassing a peptide comprising a portion of its entire amino acid residues exhibiting the same or similar effect as its entire amino acid residues.

As used herein, a renal disease may include, but is not limited to, acute and chronic renal dysfunction, while, depending on its causes, including diabetic nephropathy, hypertensive nephropathy, glomerulonephritis, pyelonephritis, interstitial nephritis, lupus nephritis, polycystic kidney disease, renal failure, drug-induced renal injury, and the like.

In some embodiments, the renal disease may be nephrotoxicity due to drugs and the like. More particularly, the drug-induced nephrotoxicity may be a nephrotoxicity induced by an anticancer agent.

The term "anticancer agent" as used herein refers to a chemotherapeutic agent used to treat tumors including malignant tumors, while the anticancer agent typically refers to an agent which intervenes in various metabolic pathways of cancer cells to exert its anticancer activity by mainly inhibiting the synthesis of nucleic acids of cancer cells. The anticancer agent utilizes the difference in susceptibility to drugs between normal cells and cancer cells, while it acts more selectively against cancer cells with relatively less toxicity to normal cells. However, normal cells are also damaged to some degree by the anticancer agent, resulting in the presence of adverse side effects. This is because the anticancer agent acts on any cell that has a rapid cell division, so it does not only act on the rapidly dividing cancer cells but also the bone marrow, gastrointestinal tract and hair follicular cells, which are also rapidly dividing cells, respectively, are also affected by the anticancer agent. The common side effects of these drugs include, are not limited to, temporary reduction of blood cells, nausea, vomiting, diarrhea, loss of appetite, and hair loss. Currently, anticancer agents used for cancer treatment are divided into six following categories according to their biochemical functional mechanisms: alkylating agents, metabolic antagonists, antibiotics, mitotic inhibitors, hormones and others.

In some embodiments, the anticancer agent includes, but is not limited to, cisplatin, doxorubicin, etoposide, paclitaxel, docetaxel, fluoropyrimidine, oxaliplatin, camptothecan, Belotecan, podophyllotoxin, vinblastine sulfate, cyclophosphamide, actinomycin, vincristine sulfate, methotrexate, bevacuzumab, thalidomide, eriotinib, gefitinib, camptothecin, Tamoxifen, Anasterozole, Gleevec, 5-fluorouracil (5-FU), Floxuridine, Leuprolide, Flutamide, Zoledronate, Vincristine, Gemcitabine, Streptozocin, Carboplatin, Topotecan, Irinotecan, Vinorelbine, hydroxyurea, Valrubicin, retinoic acid, Meclorethamine, Chlorambucil, Busulfan, Doxifluridine, Vinblastin, Mitomycin, Prednisone, Testosterone, Mitoxantron, aspirin, salicylates, ibuprofen, naproxen, fenoprofen, indomethacin, phenylbutazone, cyclophosphamide, mechlorethamine, dexamethasone, prednisolone, celecoxib, valdecoxib, nimesulide, cortisone, and corticosteroid, while there is no limitation in terms of the type of anticancer agent including a chemical compound, a hormone, an antibody and the like.

In some embodiments, the anticancer agent may be administered for treating a cancer including, but not being limited to, an ACTH-producing tumor, acute lymphoid or lymphoblastic leukemia, acute or chronic lymphocytic leukemia, acute non-lymphoid leukemia, bladder cancer, brain tumor, breast cancer, cervical cancer, chronic myelogenous leukemia, colon cancer, T zone lymphoma, endometriosis, esophageal cancer, gall bladder cancer, bladder cancer, Ewing's sarcoma, head and neck cancer, tongue cancer, Hopkins lymphoma, Kaposi's sarcoma, renal cancer, liver cancer, lung cancer, mesothelioma, multiple myeloma, neuroblastoma, non-Hodgkin lymphoma, osteosarcoma, ovarian cancer, mammary gland adenocarcinoma, prostate cancer, pancreatic cancer, colorectal cancer, penile cancer, retinoblastoma, skin cancer, stomach cancer, thyroid cancer, uterine cancer, testicular cancer, Wilms' tumor and trophoblastoma.

In some embodiments, the anticancer agent may be cisplatin.

The Neuropeptide Y may down-regulate a p53-dependent apoptosis in renal tissue or cells.

In some embodiment, the presently disclosed subject matter provides a pharmaceutical composition for preventing or treating a renal disease, the composition comprising a Y1 receptor activator as an active ingredient.

As used herein, the Y1 receptor activator may be any substance including a ligand, a chemical compound, a peptide, a protein, or a natural substance which is capable of activating the Y1 receptor signaling.

In some embodiments, the Y1 receptor activator may be a Y1 receptor agonist. The Y1 receptor agonist may include, but is not limited to Neuropeptide Y (NPY), [Leu31Pro34] NPY, BIBP3226, [D-Arg25]NPY, Peptide YY (PYY), $PYY_{3-36}$, $PYY_{1-36}$, [Leu31, Pro34]PYY, H-6375.

The pharmaceutical composition according to the present invention may further comprise pharmaceutically or physiologically acceptable carriers, excipients, and diluents.

In accordance with its purpose, the composition of the present invention may be formulated by using conventional preparation methods into various forms including oral formulations such as powders, granules, tablets, capsules, suspensions, emulsions, syrups and aerosols, and parenteral formulations such as sterilized injection solutions. The composition of the present invention can be administered in various routes, such as orally, intravenously, intraperitoneally, subcutaneously, rectally, topically, and the like. Examples of suitable carriers, excipients and diluents that may be contained in such compositions include lactose, dextrose, sucrose, sorbitol, mannitol, xylitol, erythritol, maltitol, starch, acacia rubber, alginate, gelatin, calcium phosphate, calcium silicate, cellulose, methyl cellulose, amorphous cellulose, polyvinyl pyrrolidone, water, methyl hydroxybenzoate, propyl hydroxybenzoate, talc, magnesium stearate, mineral oil and the like. The composition may further contain a filler, an anti-coagulant, a lubricant, a wetting agent, a flavoring agent, an emulsifying agent, an antiseptic, and the like.

A solid formulation for oral administration may include tablets, pills, powders, granules, capsules and the like, while the solid formulation may contain at least one excipient, such as starch, calcium carbonate, sucrose, lactose, gelatin and the like. In addition to simple excipients, lubricants such as magnesium stearate and talc may be also used.

A liquid formulation for oral administration may include suspension, solution, emulsion, syrup and the like, while the liquid formulation may contain various excipients such as a wetting agent, a sweetening agent, a fragrance, a preservative and the like in addition to commonly-used simple diluents such as water and liquid paraffin.

Formulations for parenteral administration may include sterilized aqueous solutions, non-aqueous solutions, suspensions, emulsions, freeze-dried preparations, and suppositories. Examples of non-aqueous solutions and suspensions may include propylene glycol, polyethylene glycol, vegetable oil such as olive oil, injectable ester such as ethyl oleate, and the like. Base materials for injections may include conventional additives such as solubilizers, isotonic agents, suspending agents, emulsifying agents, stabilizing agents and preservatives.

As used herein, the term "administration" means providing a pre-determined substance to a patient by any suitable method, while the administration route of the composition according to the present invention may include any typical oral or parenteral route as long as the administered substance may reach a desired destination such as a desired tissue.

In some embodiments, the pharmaceutical composition according to the present invention may be administered in combination with at least a conventionally available agent for treating a renal disease.

The composition of the present invention may be administered in a pharmaceutically effective amount.

As used herein, the term "a pharmaceutically effective amount" means an amount sufficient to treat a disease at a reasonable benefit to risk ratio applicable to medical treatment, while the level of an effective dosage will depend on the type and severity of a disease, the activity of a drug, the sensitivity to a drug, the time of administration, the route of administration, the rate of release, the duration of the treatment, factors including co-administered drugs, and other factors well known in the medical arts. The composition of the present invention can be administered in a single dosage or multiple dosages as an individual therapeutic agent or in combination with other therapeutic agents, while being administered sequentially or simultaneously with other conventional therapeutic agents. It is important to take into account all of the above-mentioned factors and administer an amount that can achieve the maximum effect in a minimal amount without adverse side effects, which can be easily determined by those skilled in the art.

In particular, the effective amount of the active ingredient in the composition according to the present invention may vary depending on the age, gender and weight of the subject. In some embodiments, it may be in the range of about 0.01 µg to about 10,000 mg per kilogram of body weight per day, while being in the range of about 0.1 µg to about 500 mg per kilogram of body weight per day. In further embodiments, it may be in the range of about 1 to about 50 mg per kilogram of body weight per day. In other embodiments, about 1 to about 10 mg per kilogram of body weight of the active ingredient may be administered daily, every other day, or one to three times a day in a divided manner.

The dose may be increased or decreased depending on the route of administration, the severity of disease, sex, weight, age of the subject and the like. One skilled in the art where the presently described subject matter belongs will be able to determine the appropriate effective dose of the composition according to the present invention in view of the above mentioned various factors. The pharmaceutical composition according to the present invention is not particularly limited in terms of the formulation, administration route, and administration method as long as the effect of the present invention is exhibited.

In some embodiment, the presently disclosed subject matter provides a food composition for preventing or ameliorating a renal disease, the composition comprising Neuropeptide Y as an active ingredient.

The food composition according to the present invention includes all forms such as functional food, nutritional supplement, health food and food additives.

The food composition of the present invention can be prepared in various forms according to conventional methods known in the art. In some embodiments, the food composition of the present invention includes various forms such as pills, powders, granules, tablets, capsules and liquid preparations. Foods to which the composition of the present invention can be added include, for example, meats, sausages, breads, chocolates, candies, snacks, confectioneries, pizzas, ramen, gums, ice creams, soups, beverages, teas, drinks, alcoholic beverages and vitamin mix.

In some embodiments, as a health food, the food composition of the present invention may be prepared in the form of tea, juice or drink, and may be ingested in a drinkable form, or in a granulated, encapsulated or powdered form. In addition, the food composition of the present invention may be prepared in the form of a composition by mixing with known substances or active ingredients which are known to be effective for ameliorating, improving or treating a renal disease.

Functional foods may be prepared by containing the food composition of the present invention in beverages (including alcoholic beverages), fruits and their processed foods (such as canned fruits, bottled fruits, jam, marmalade), fish, meat and processed foods (such as ham, sausage, corn beef), breads and noodles (such as udon, buckwheat noodles, ramen, spaghetti, macaroni), juice, various drinks, cookies, taffy, milk products (such as butter and cheese), edible vegetable oil, margarine, vegetable protein, retort food, frozen food, various seasonings (such as soybean paste, soy sauce, sauce) and the like.

There are no particular restrictions on other ingredients to be included as an essential ingredient in the food composition of the present invention, other than a food composition containing at least one selected from the group consisting of bee venom, melitin and apamin as an active ingredient. Like other conventional food products, various herbal extracts, food-aid additives, or natural carbohydrates may be further added. The food-aid additive may be also added, while the food-aid additive may be a conventional food-aid additive in the art, for example, a flavoring agent, a coloring agent, a filling agent, a stabilizing agent and the like. The examples of the natural carbohydrates may include monosaccharides such as glucose and fructose; disaccharides such as maltose and sucrose; polysaccharides such as such as dextrin and cyclodextrins; and sugar alcohols such as xylitol, sorbitol and erythritol. As a flavoring agent, a natural flavoring agent (for instance, thaumartin, and stevia extract such as Rebaudioside A and Glycyrrhizin) and a synthetic flavoring agent (for instance, saccharin and aspartame) can be advantageously used, other than the above mentioned ones. In addition to the above, the food composition of the present invention may contain various nutrients, vitamins, minerals (electrolytes), flavoring agents such as synthetic and natural flavoring agents, coloring agents and thickening agents (cheese, chocolate etc.), pectic acid and its salts, alginic acid and its salts, organic acids, protective colloid thickeners, pH adjusting agents, stabilizers, preservatives, glycerin, alcohols, carbonating agents used in carbonated beverages and the like. In addition, fruit pulps may be contained in order to prepare natural fruit juices, fruit juice drinks and vegetable drinks. These ingredients may be used independently or in combination.

In some embodiments, the content of the food composition according to the present invention is around 0.01 to 50% by weight of the total weight of the final food. In some embodiments where the food composition of the present invention is used in the form of a food additive, it may be used in the form of powder or concentrate.

In some embodiments, the presently disclosed subject matter provides a food composition for preventing or ameliorating a renal disease, the composition comprising a Y1 receptor activator as an active ingredient.

In some embodiments, the presently disclosed subject matter provides a method for treating or reducing an anticancer agent-induced nephrotoxic injury, the method comprising the step of administering a Y1 receptor activator in an amount effective to treat or reduce the anticancer agent-induced nephrotoxic injury in a subject.

In some embodiments, the Y1 receptor activator is a substance selected from the group consisting of a ligand, a chemical compound, a peptide, a protein and a natural substance which is capable of activating a Y1 receptor signaling.

As used herein, the terms "polypeptide", "peptide", and "protein" are interchangeable and are defined to mean a biomolecule composed of amino acids linked by a peptide bond.

In some embodiments, the Y1 receptor activator is a Y1 receptor agonist.

In some embodiments, the Y1 receptor agonist is at least one selected from the group consisting of Neuropeptide Y (NPY), [Leu31Pro34]NPY, [D-Arg25]NPY, Peptide YY (PYY), $PYY_{3-36}$, $PYY_{1-36}$, and [Leu31, Pro34]PYY.

In some embodiments, the Y1 receptor agonist is Neuropeptide Y (NPY) or [Leu31Pro34]NPY. In another embodiments, Neuropeptide Y (NPY) may refer to Neuropeptide Y (NPY) represented by SEQ ID NO: 1.

In some embodiments, the Y1 receptor agonist is Peptide YY (PYY), $PYY_{3-36}$, $PYY_{1-36}$, or [Leu31, Pro34]PYY. In another embodiments, Peptide YY (PYY) may refer to Peptide YY (PYY) represented by SEQ ID NO: 2.

As used herein, the "Neuropeptide Y (NPY)" and "Peptide YY (PYY)" may include functional equivalents thereof.

More specifically, the functional equivalents of the Neuropeptide Y (NPY) or Peptide YY (PYY) as used herein refer to polypeptides comprising the amino acid sequence having at least 70% amino acid sequence homology (i.e., identity), preferably at least 80%, more preferably at least 85%, further more preferably at least 90% and most preferably at least 95%, for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and more to Neuropeptide Y (NPY) or Peptide YY (PYY), as a result of the addition, substitution or deletion of some amino acid residues of Neuropeptide Y (NPY) or Peptide YY (PYY), while exhibiting substantially identical physiological activity to Neuropeptide Y (NPY) or Peptide YY (PYY).

In some embodiments, the functional equivalents of Neuropeptide Y (NPY) include, but are not limited to, [Leu31Pro34]NPY or [D-Arg25]NPY.

In some embodiments, the functional equivalents of Peptide YY (PYY) include, but are not limited to, $PYY_{3-36}$ or [Leu31, Pro34]PYY.

In some embodiments, the Y1 receptor activator such as Neuropeptide Y (NPY) or [Leu31Pro34]NPY inhibits p53-dependent apoptosis.

In some embodiments, the anticancer agent is at least one selected from the group consisting of cisplatin, doxorubicin, etoposide, paclitaxel, docetaxel, fluoropyrimidine, oxaliplatin, campthotecan, Belotecan, podophyllotoxin, vinblastine sulfate, cyclophosphamide, actinomycin, vincristine sulfate, methotrexate, bevacuzumab, thalidomide, eriotinib, gefitinib, camptothecin, Tamoxifen, Anasterozole, Gleevec, 5-fluorouracil (5-FU), Floxuridine, Leuprolide, Flutamide, Zoledronate, Vincristine, Gemcitabine, Streptozocin, Carboplatin, Topotecan, Irinotecan, Vinorelbine, hydroxyurea, Valrubicin, retinoic acid, Meclorethamine, Chlorambucil, Busulfan, Doxifluridine, Vinblastin, Mitomycin, Prednisone, Testosterone, Mitoxantron, aspirin, salicylates, ibuprofen, naproxen, fenoprofen, indomethacin, phenylbutazone, cyclophosphamide, mechlorethamine, dexamethasone, prednisolone, celecoxib, valdecoxib, nimesulide, cortisone, and corticosteroid.

As verified by the following Examples, the present inventors found that the Y1 receptor activator/agonist (such as Neuropeptide Y or its derivatives) according to the present invention effectively restores renal injury, and in particular, can down-regulate the apoptosis of kidney cells caused by anticancer agent-induced nephrotoxicity, suggesting that it can be useful as a therapeutic agent for treating or reducing an anticancer agent-induced nephrotoxic injury.

As used herein, the term "effective amount" refers to an amount that, when administered to a subject, leads to the effect of improvement, amelioration, reduction, prevention, or treatment of an anticancer agent-induced nephrotoxic injury. The effective amount varies depending on the route of administration, the severity of disease, sex, weight, age of the subject and the like. One skilled in the art where the presently described subject matter belongs will be able to determine the appropriate effective amount of the Y1 receptor activator/agonist (such as Neuropeptide Y or its derivatives) according to the present invention to be administered in view of the above mentioned various factors.

The term "subject" refers to an animal, preferably a mammal which especially includes a human, while including animal-derived cells, tissues, organs and the like. The subject may be a patient in need of the above mentioned effect.

As used herein, the term "treating" broadly refers to the improvement of an anticancer agent-induced nephrotoxic injury, or the amelioration of symptoms derived from an anticancer agent-induced nephrotoxic injury, while including, without limitation, curing, substantially preventing, and improving said nephrotoxic injury conditions; and relieving, curing or preventing one or more of the symptoms resulting from said nephrotoxic injury.

In some embodiments, the presently disclosed subject matter provides a method for screening an agent for treating or reducing an anticancer agent-induced nephrotoxic injury, the method comprising
(a) applying a candidate material to a test sample of renal tissues or cells; and
(b) identifying a Y1 receptor signaling in the test sample of renal tissues or cells.

EXAMPLES

Hereinafter, the presently described subject matter will be described in more detail with reference to following Examples. The following Examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Example 1

Samples and Methods 1-1. Mice

Six- to eight-weeks old male or female C57BL/6 mice were purchased from the Jackson laboratory. A block randomization method was used to divide these animals into experimental groups. In order to eliminate bias, investigators were blinded during data collection and analysis. The mice were housed under a 12 hour day-night cycle. They were provided with free access to water and food pellets. This animal study was approved by the Kyungpook National University Institutional Animal Care and Use Committee.

1-2. Drug Treatment

Cisplatin (Sigma P4394) at 15 mg per kg body weight was used to induce renal injury. To assess renal protection from cisplatin, mice were intraperitoneally injected with Neuropeptide Y (NPY) (Bachem; 50 ug per kg body weight, H-6375) or Y1 agonist [Leu31Pro34]NPY (Bachem; 50 ug per kg body weight, H-3306) daily for 3 days (See FIG. 1a). Three days later, kidneys were collected and analyzed.

1-3. Creatinine and BUN Assays

To monitor renal function, plasma levels of BUN and creatinine were determined using commercially available kits as described previously (See Pabla N et al., J Clin Invest 121, 2709-2722, 2011).

1-4. Histology, immunohistochemistry, and Morphological Assessment

Formaldehyde-fixed kidneys were dehydrated using graded alcohol series and paraffinized. Paraffin sections of 5 µm were stained with hematoxylin and eosin (H&E). Each parameter was determined for at least 6 different animals. TUNEL assays were performed using In Situ Cell Detection Kit, Fluorescein (Roche Diagnostic) according to the manufacturer's instructions. A pathologist quantified kidney damage in a double blinded manner using renal damage score, as previously described (See Jiang M et al., Am J Physiol Renal Physiol 287, F1140-1147, 2004). Briefly, tissues were stained with H&E. The degree of morphological involvement in renal dysfunction was determined using light microscopy.

The following parameters were chosen as indicators of morphological damage to the kidney after cisplatin injection: brush border loss, red blood cell extravasation, tubule dilation, tubule degeneration, tubule necrosis, and tubular cast formation. Each parameter was determined for at least five different animals.

1-5. Western Blotting

Samples were immunoblotted as previously described (See Santos-Carvalho A et al., Cell Death Dis 4, e636, 2013). Primary antibodies against the following proteins were used: P53(mouse, 1: 1000, Cell Signaling Technologies, 2524), Bax (rabbit, 1: 1000, Cell Signaling Technologies, 2772), Bcl2 (rabbit, 1: 1000, Cell Signaling Technologies, 5114S), and β-actin (1: 1000, Santa Cruz, SC-1615). Densitometric quantification was performed using Image J software (US National Institutes of Health).

1-6. Quantitative Real-Time PCR

Real time RT-PCR was performed as previously described (See Hu L et al., BMB Rep 48, 583-588, 2015). RNA was extracted from bone marrow using the RNeasy Lipid Tissue Mini kit (Qiagen) according to the manufacturer's instructions. cDNA was synthesized from 5 µg of total RNA using RNA to cDNA EcoDry™ Premix (Oligo dT) from Clontech. Quantitative real-time PCR was performed using Corbett research RG-6000 real-time PCR instrument. The following primers were used:

Neuropeptide Y
(NPY, Forward:
5'-AGATCCAGCCCTGAGACACT-3',
Reverse:
5'-AGATGAGGGTGGAAACTTGG-3'), Y1R
(Y1 receptor, Forward:
5'-TGTCACCAACATTCTGATCG-3',
Reverse:
5'-GATGAGAACCAGCGAGAAAA-3'), Y2R
(Y2 receptor, Forward:
5'-TGCAGACCTCCCATTGTATT-3',
Reverse:
5'-CAATCCAAGCATCGGTAATC-3'), Y4R
(Y4 receptor, Forward:
5'-TAGTCGTGTCTGGGCTTTTC-3'
Reverse:
5'-AGCAAAGGGCTAAACCATCT-3'), Y5R
(Y5 receptor, Forward:
5'-GGGCTCTATACATTTGTAAGTCTTCTG-3',
Reverse:
5'-CATGGCTTTGCCGAACATCCACTGATC-3'), Y6R
(Y6 receptor, Forward:
5'-GGAGGGATGGTTATTGTGAC-3',
Reverse:
5'-GTTGTTGCTCTTGCCACTGG-3'), P53 (Forward:
5'-TGAAACGCCGACCTATCCTTA-3',
Reverse:
5'-GGCACAAACACGAACCTCAAA-3'), Bax
(Forward:
5'-TTGCTACAGGGTTTCATCCA-3',
Reverse:
5'-CATATTGCTGTCCAGTTCATCTC-3'), Noxa
(Forward:
5'-ACTGTGGTTCTGGCGCAGAT-3',
Reverse:
5'-TTGAGCACACTCGTCCTTCAA-3'), Puma
(Forward:
5'-ATGCCTGCCTCACCTTCATCT-3',
Reverse:
5'-AGCACAGGATTCACAGTCTGGA-3'), Bcl2
(Forward:
5'-TTATAAGCTGTCACAGAGGGG-3',
Reverse:
5'-GAACTCAAAGAAGGCCACAATCCTC-3'), Mcl1
(Forward:
5'-GAGGAGGAAGAGGACCTATACC-3',
Reverse:
5'-AGTTTCTGCTAATGGTTCGATGAAG-3'),
and GAPDH
(Forward:
5'-TGGCAAAGTGGAGATTGTTGCC-3',
Reverse:
5'-AAGATGGTGATGGGCTTCCCG-3').

1-7. Statistical Analysis

Comparisons between two groups were performed using Student's t-test. In cases where more than two groups were compared to each other, one way analysis of variance (ANOVA) was conducted, followed by Tukey's HSD test. All statistical analyses were performed using SPSS statistical software. A P value of less than 0.05 was considered statistically significant.

Example 2

Results 2-1. The In Vivo Effect of NPY in Preventing and Treating Cisplatin-Induced Kidney Injury As mentioned above, cisplatin-induced nephrotoxicity is a common side effect of clinical chemotherapy for cancer patients. To determine whether Neuropeptide Y (NPY) could prevent or ameliorate cisplatin-induced nephrotoxicity, mice were injected with Neuropeptide Y (NPY) or PBS after induction of renal injury by cisplatin (See FIG. 1a). The present inventors first analyzed changes in the expression levels of Neuropeptide Y (NPY) which was induced by cisplatin in the kidney.

Figure 1B:
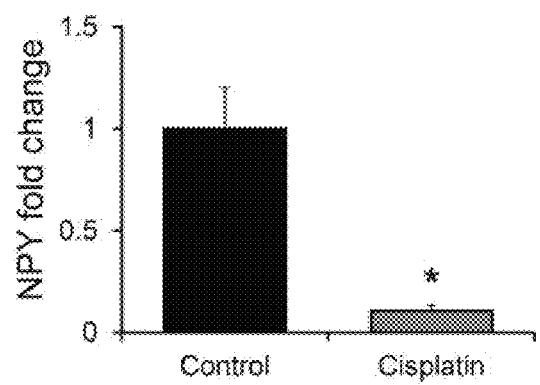
Figure 1C:
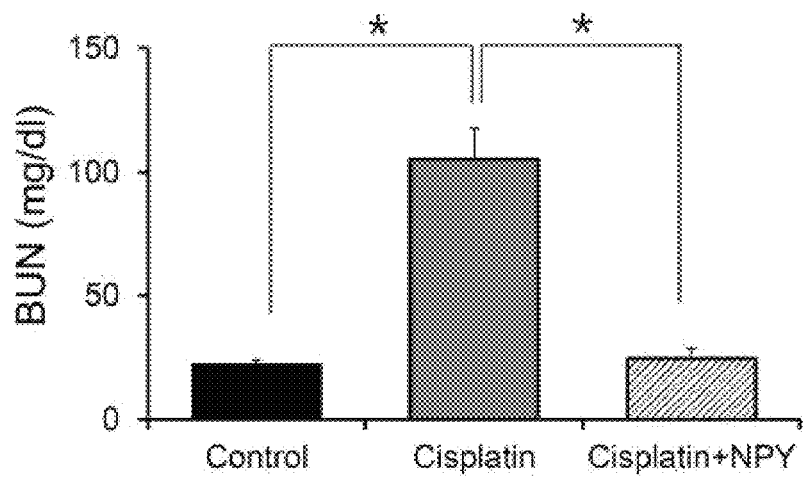
Figure 1D:
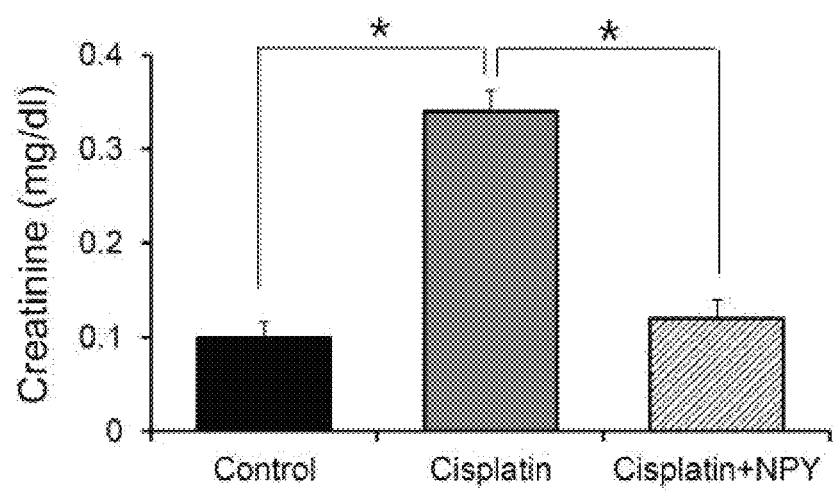
Figure 1E:
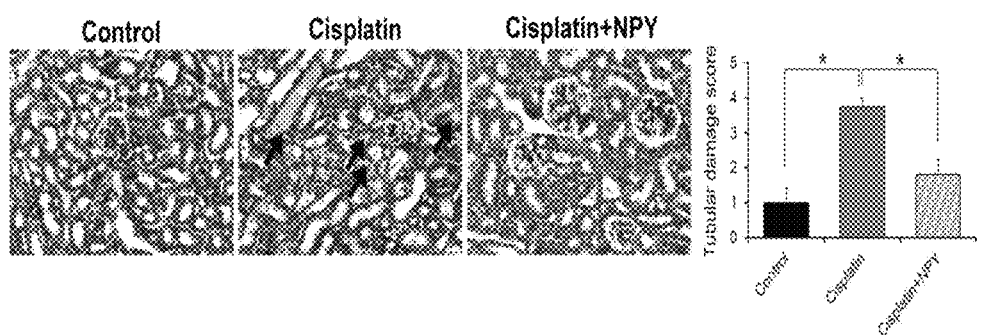

The mRNA levels of Neuropeptide Y (NPY) in renal cells were significantly decreased in cisplatin-treated mice, compared to those in PBS-treated controls (See FIG. 1b). Plasma concentrations of blood urea nitrogen (BUN) and creatinine, which are indicators for loss of kidney function, respectively, were significantly ($P<0.05$) elevated in cisplatin-treated mice. However, they were decreased by Neuropeptide Y (NPY) treatment (See FIGS. 1c and 1d). Histologic analysis with hematoxylin and eosin (H&E) staining showed that the increase in apoptotic tubular cells in the renal cortex induced by cisplatin treatment was diminished by Neuropeptide Y (NPY) treatment (See FIG. 1e). These results suggest that NPY can protect renal cells against cisplatin-induced dysfunction.

2-2. The Effect of NPY in Down-Regulating p53-Dependent Apoptosis Pathway in Cisplatin-Induced Renal Injury It is known that renal apoptosis is a main pathogenesis in kidney injury caused by cisplatin treatment. To determine whether Neuropeptide Y (NPY) diminishes cisplatin-induced apoptosis in the kidney, renal apoptosis was examined by TUNEL assay.

Figure 2A:
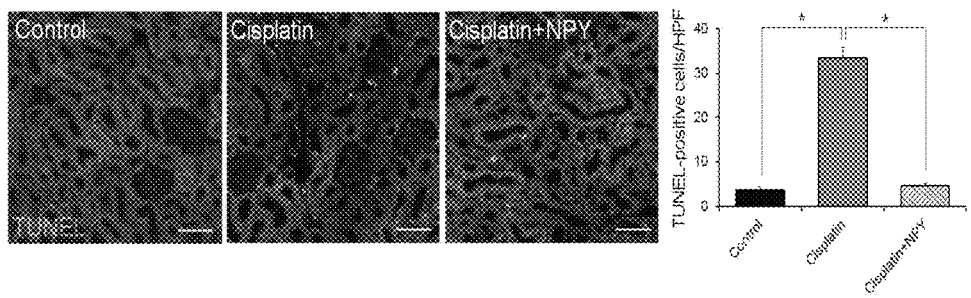
FIGS. 2A-2C show the down-regulation of genes in the p53-dependent apoptosis pathway after Neuropeptide Y (NPY) treatment.
Figure 2B:
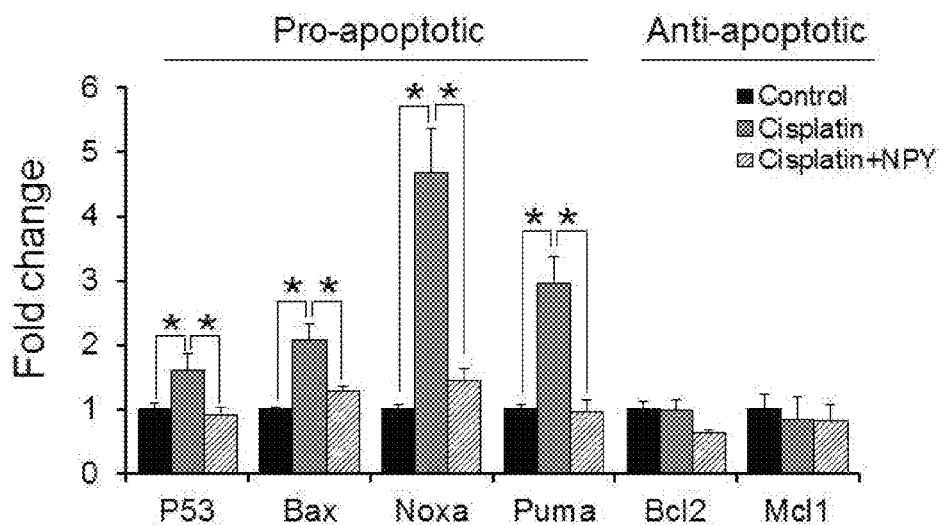
Figure 2C:
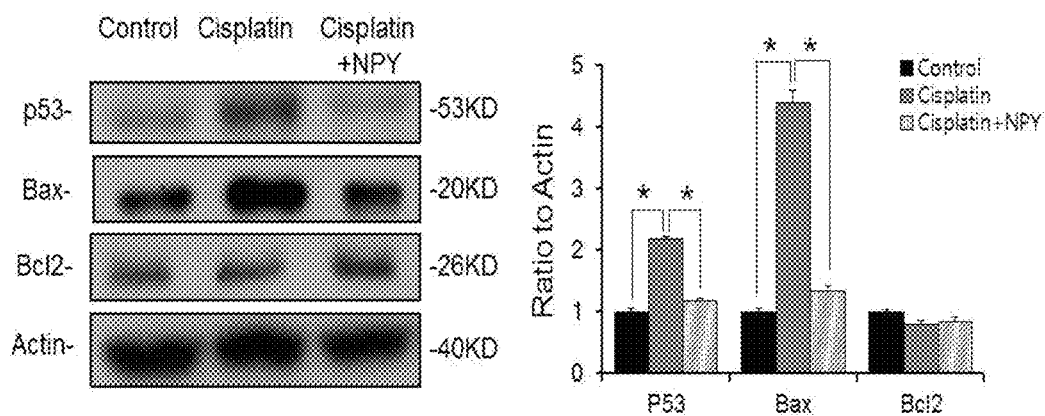

It was found that Neuropeptide Y (NPY) treatment led to a decrease in apoptotic cells in the kidney (See FIG. 2a). Next, the expression levels of key modulators of the p53-dependent apoptosis pathway was evaluated. It was found that the expression levels of p53 and pro-apoptotic genes such as Bax, Noxa, and Puma were increased in cisplatin treated mice, whereas being decreased in Neuropeptide Y (NPY) treated mice (See FIGS. 2b and 2c). Taken together, these results indicate that Neuropeptide Y (NPY) could abrogate cisplatin-induced renal apoptosis via down-regulating the expression of the genes involved in the p53-dependent apoptosis pathway.

Figure 3A:
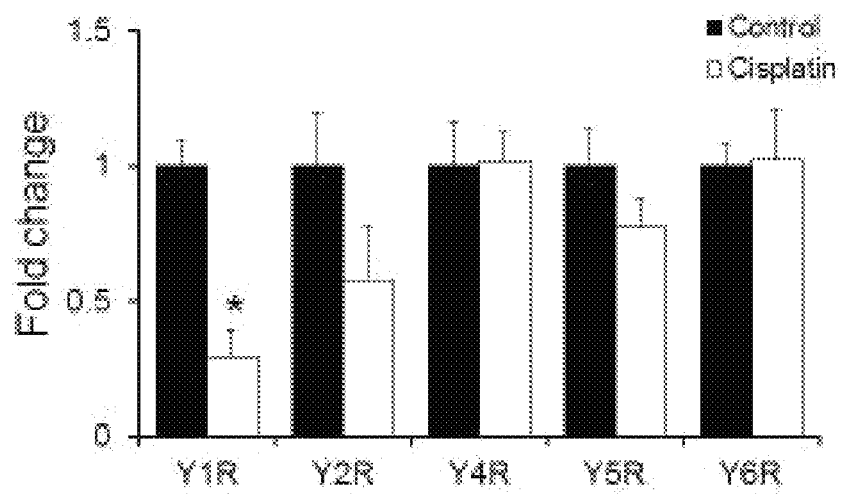
FIGS. 3A-3G demonstrate that NPY ameliorates cisplatin-induced renal injury through Y1 receptor signaling.

2-3. The Effect of NPY/Y1 Receptor Pathway in Protecting the Kidney Against Cisplatin-Induced Nephrotoxicity Subsequently, the present inventors determined which receptor(s) was associated with the protective effect of Neuropeptide Y (NPY) in renal apoptosis. First, the expression levels of Neuropeptide Y (NPY) receptors in the kidney of cisplatin treated mice were evaluated. Among different receptors, the expression level of Y1 receptor was significantly decreased after cisplatin treatment (See FIG. 3a). Therefore, the present inventors focused on the Y1 receptor in order to examine the mechanism of NPY-mediated protection in cisplatin-induced renal injury.

Figure 3B:
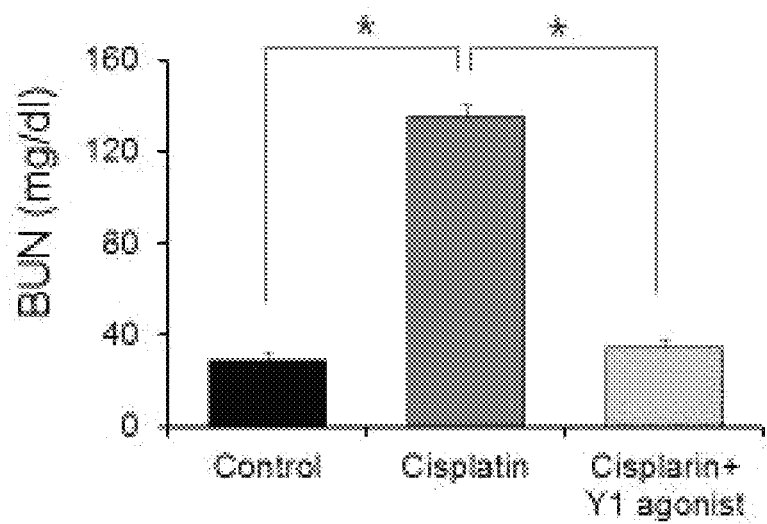
Figure 3C:
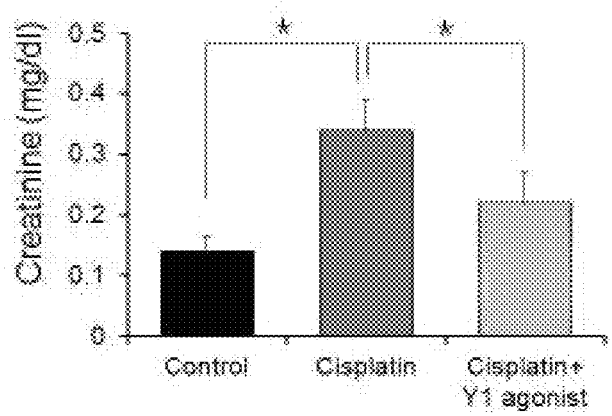
Figure 3D:
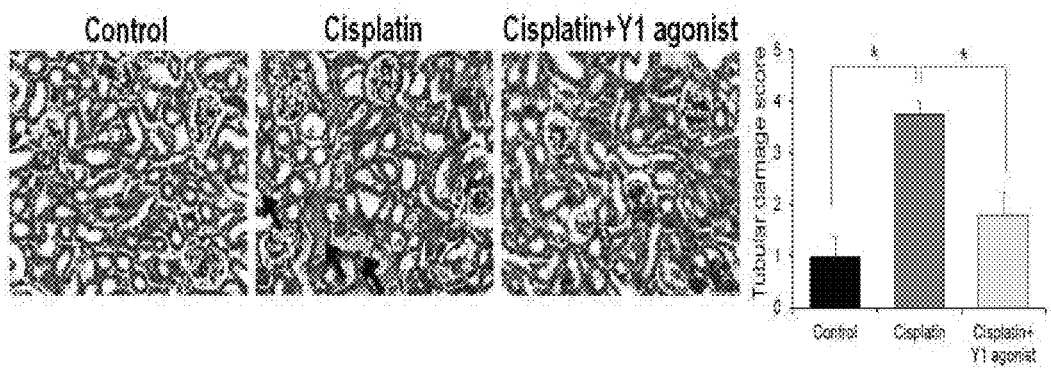
Figure 3E:
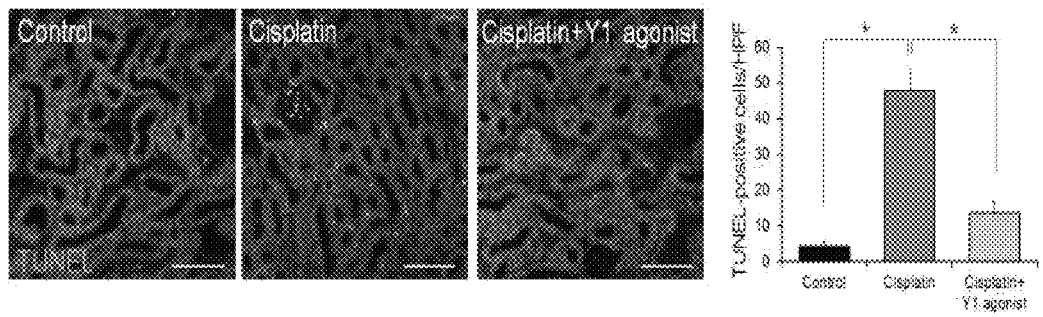
Figure 3F:
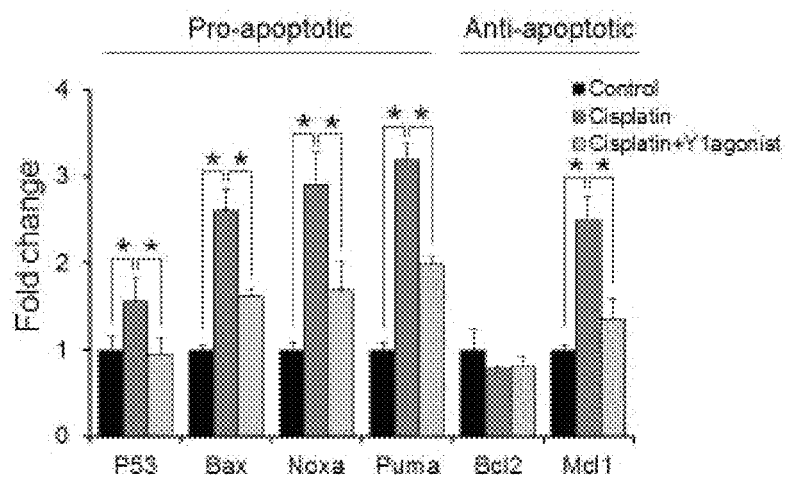
Figure 3G:
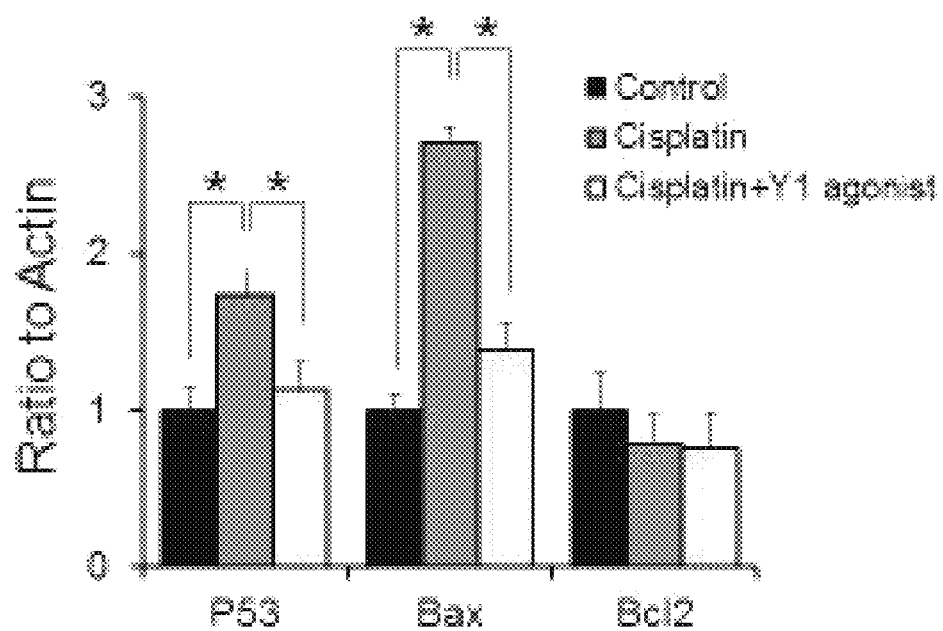

To confirm the renoprotection of Neuropeptide Y (NPY) through Y1 receptor signaling, a Y1 agonist Y1 agonist (Bachem, H-3306) was injected into cisplatin-treated mice as described in FIG. 1a. It was confirmed that creatinine and BUN levels were reduced in Y1 agonist treated mice, compared to those in cisplatin-treated mice (See FIGS. 3b and 3c). Mice treated with cisplatin demonstrated various injuries, whereas mice infused with the Y1 agonist showed significantly reduced renal injury (See FIG. 3d). Moreover, it was found that the Y1 agonist decreased cisplatin induced renal injury (See FIG. 3e). The present inventors also determined the expression levels of apoptosis-related genes and proteins. Similar to the results observed with Neuropeptide Y (NPY) treatment, it was verified that the Y1 agonist suppressed the expression levels of p53 and pro-apoptotic genes such as Bax, Noxa, and Puma (See FIG. 3f). Taken together, these results strongly suggest that Neuropeptide Y (NPY) can provide renoprotection against cisplatin-induced kidney injury through Y1 receptors.

What is claimed is:

1. A method for treating or reducing an anticancer agent-induced nephrotoxic injury in a subject, the method comprising the step of administering a Y1 receptor activator in an amount effective to treat or reduce the anticancer agent-induced nephrotoxic injury in a subject, wherein the Y1 receptor activator is Neuropeptide Y (NPY) or [Leu31 Pro34]NPY, wherein the anticancer agent is at least one selected from the group consisting of cisplatin, carboplatin and oxaliplatin.

2. The method of claim 1, wherein the Y1 receptor agonist inhibits p53-dependent apoptosis.

3. The method of claim 1, wherein the anticancer agent is cisplatin.

* * * * *